United States Patent [19]

Huntress

[11] 4,029,169
[45] June 14, 1977

[54] ACOUSTIC YOKE

[75] Inventor: Charles B. Huntress, Orange, Calif.

[73] Assignee: Electronic Engineering Company of California, Santa Ana, Calif.

[22] Filed: Jan. 28, 1976

[21] Appl. No.: 653,052

[52] U.S. Cl. .................... 181/135; 181/131
[51] Int. Cl.² .......................... A61B 7/02
[58] Field of Search ............ 181/131, 135, 137; 179/1 ST

[56] References Cited

UNITED STATES PATENTS

| 2,738,850 | 3/1956 | Tooker | 181/135 |
| 3,217,831 | 11/1965 | Scanlon | 181/135 |
| 3,547,219 | 12/1970 | Bothos | 181/135 |
| 3,730,290 | 5/1973 | Scanlon | 181/135 |
| 3,776,362 | 12/1973 | Rice | 181/135 |
| 3,899,044 | 8/1975 | Stumpf et al. | 181/131 |
| 3,918,550 | 11/1975 | Milani | 181/135 |
| 3,934,674 | 1/1976 | Shore et al. | 181/135 |

Primary Examiner—Stephen J. Tomsky
Attorney, Agent, or Firm—Harry R. Lubcke

[57] ABSTRACT

A "U" shaped yoke for retaining a pair of ear couplers to the ears of an individual at a minimum effective pressure in an acoustic system. A pair of right-angle horns carry the ear couplers and are rotatively mounted at the extremities of the U to allow optimum adjustment of the couplers to the ears of the wearer. The structure is assembled without adhesive and may be disassembled.

5 Claims, 2 Drawing Figures

ACOUSTIC YOKE

BACKGROUND OF THE INVENTION

This invention pertains to a stethoscope-like device for conveying sound to the ears of an individual.

The stethoscope, long used by doctors, is a basic means for conveying sound to the ears of an individual while excluding ambient sounds.

More recently stereophonic sound has been separately conveyed to each ear of an individual by means of a pair of flexible tubes in a stethoscope arrangement. Frequently such sound is listened-to for hours, as on an airplane trip. The matter of comfort to the wearer thus becomes of great importance.

The prior art has made only nominal progress in providing such comfort.

A double form of yoke has been provided, having a horizontal swivel fitment at each extremity of the yoke. The fitment rotates in the yoke proper, but an external flexible tube on the second part of the yoke is employed to convey the sound from the point of origin through the fitment, being structurally independent of the yoke proper. The rotation of the fitment is limited to about 90° because the external flexible tube must radially accommodate to the position chosen. It is likely that the usual elasticity of the external flexible tube acts to return the fitment to that angle where the stress upon the tube is a minimum. This may not be the optimum orientation for best acoustic performance for the wearer.

Another double yoke sound tube head set has been proposed in which the sound tube is again separated from the yoke proper, but there is no provision for swiveling the ear coupler with respect to the ear.

A single yoke sound head set is also known that functionally parallels the usual doctor's stethoscope, but embodies the structure that does not contribute to the comfort of the wearer.

A single over-the-head "yoke" is also known that first conveys monaural sound to one ear and thereafter to the other ear through the hollow interior of a curved resilient headband that constitutes the yoke.

SUMMARY OF THE INVENTION

A light-weight unified stereophonic yoke is assembled without adhesive and may be disassembled by merely the fingers. Sound couplers to the ear are each mounted upon right-angled horns that swivel within each extremity of the U shaped yoke. This allows optimum acoustic coupling and as much as 360° rotation for optimum fit to the ears of any individual; also for inspection or other manipulation.

The horns snap in and out of the yoke by the application of finger pressure, for cleaning or sterilization, for replacement, and for convenience of assembly during manufacture.

A curved internal bore is provided within each horn to retain good acoustic frequency response.

DESCRIPTION OF THE PREFERRED EMBODIMENT

U shaped yoke 1 is fabricated of a lightweight plastic material, of which polypropylene is one example. This material remains constant in flexibility with time. Thus, it is suitable for maintaining a desired relatively light pressure upon the ears throughout the life of the device, and despite repeated cleaning or sterilization procedures.

The amplitude of this pressure may be 25 grams for the particular highly flexible ear coupler disclosed in a copending application assigned to the same assignee herein entitled, "Ear Coupler", having been filed on Dec. 22, 1975, Ser. No. 643,571.

The amplitude of the pressure is determined by the shape of the mold employed in providing an over-all rounded U shape, such as brings the extremities of the U closer together than the separation of the ears upon the wearer's head; also upon the stiffness of the yoke, as determined by the cross-sectional area thereof.

Figure 1:
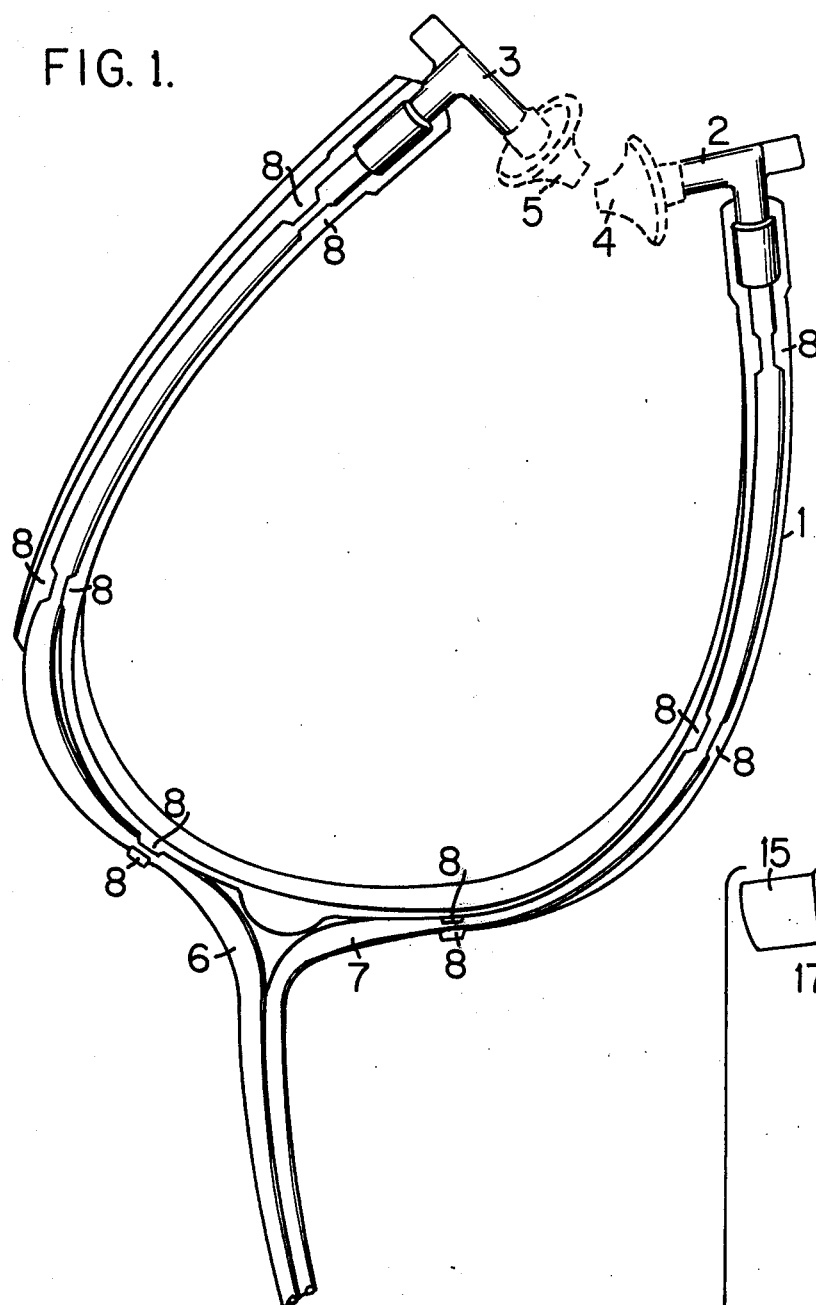
FIG. 1 is a front view of the assembled yoke, in perspective.

In the embodiment shown in FIG. 1 the over-all rounding of the U is chosen to bring the extremities of the U approximately half as far apart as the maximum separation between the arms of the U half way down from the extremities to the bottom of the U.

The cross-section of the yoke may have the shape of a U in a square font of type, with an extent of about 1 cm at the bottom and on both side of the U. The thickness is about 2 mm for each of these three parts of the U. The fourth, or front side, is open. Preferably the external corners of the U cross-section are rounded to prevent irritation to any part of the body found likely to be contacted by the yoke. Of course, the whole bottom of the cross-section of the U may be rounded.

The yokes of the prior art have frequently been of one piece, with a right-angle bend at each extremity of the U to hold ear couplers of some sort.

It has been found superior by acoustic test to employ separate revolvable horns 2, 3, one at each extremity of the U. This allows ear couplers 4 and 5 to assume the most advantageous orientation with respect to the concha and the canal of each ear. This preserves optimum frequency response of the sound. This increases the understandability of motion picture dialog and retains the high fidelity of stereophonic or monaural music.

The ear couplers are shown dotted in FIG. 1, since they are not a part of this invention, other than being a preferred type of some sort of ear coupler that is required.

Figure 2:
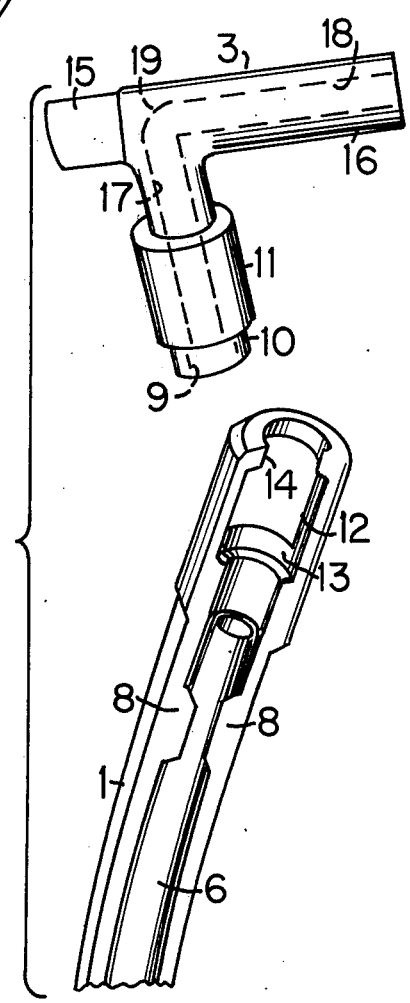
FIG. 2 is an exploded view of the upper portion of one side of the yoke and the swivel ear horn that assembles into it, in perspective.

The structure of an extremity of the yoke 1 and horn 3 is shown in the exploded view of FIG. 2.

The flexible plastic tubing 6, there shown, is one of two such tubes 6 and 7, that convey sound from a known stereophonic or monaural acoustic plug, not shown, to an ear.

A suitable material for the tubing is a polyvinylchloride (PVC).

The tubing is mechanically nested within yoke 1 by six pairs of tabs 8. The flexibility of the tubing allows such nesting and also removable option when required by ordinary finger dexterity.

A bore 9 within bottom boss 10 of horn 3 slips over the tubing to form a joint to the upper extremity of tubing 6 that is acoustically tight.

A larger diameter boss 11 is formed above bottom boss 10 of horn 3. Boss 11 fits into socket 12 at the upper extremity of yoke 1. The socket is formed to have a circumference greater than a semicircle and the yoke material has sufficient resilience to allow boss 11 to be forced into socket 12 by finger pressure. The two parts thereafter remain together until separated by finger pressure.

The cylindrical fit between the horn and the yoke is such that the friction between the two maintains any orientation of the horn that is chosen by the wearer.

A lower shoulder 13 and an upper shoulder 14 secure horn 3 against axial displacement.

Externally the horn has projection 15 included, colinear but opposite to the right-angle extremity 16 that receives coupler 5. This projection is for finger manipulation and orientation of the horn by the wearer, before, during, or after insertion of the coupler into the ear, insofar as this might be necessary.

Horn 3 has a continuous bore; being 17 in the vertical portion and 18 in the horizontal portion. This allows acoustic connection from tube 6 to and through ear coupler 5.

It was found by acoustic measurement that a curved outer radius 19 for this bore as it passes from portions 17 to 18, maintained proper frequency response of the sound that passed through the bore. This was an improvement over a prior rectilinear junction at this point.

It is possible to mold this curved outer radius and a commensurate smaller radius at the sides of this change in direction of the bore. However, it is not possible to mold a curve at the inner portion, but this relatively small rectangularity was found to have only a minor acoustic influence on the frequency characteristic of the sound.

Certain proportions may be varied in the practice of the invention; as the length of portion 18, the axial length of boss 11, and the nature and extent of projection 15.

The yoke of this invention is usable, of course, for monaural sound by merely supplying the same sound to both tubes 6 and 7.

I claim:
1. A yoke for retaining a pair of acoustic ear couplers in the ears of a wearer, comprising;
 a. a U shaped in cross-section yoke (1) to retain a pair of flexible tubes (6 & 7),
 b. an open surmounting socket (12) upon each extremity of the U shaped yoke,
 each said socket having a circumference greater than a semicircle, and
 c. a hollow ear horn (3), which has a boss (11) that rotatably and removably fits within a said socket (12),
 coaxially accepts a said flexible tube (6 or 7) at the boss end,
 and accepts a said ear coupler (5) at the other end.
2. The yoke of claim 1, in which;
 a. each ear horn has an acoustic bore of uniform diameter, and
 b. each ear horn has a curved internal surface (19), where the acoustic bore (17, 18) passes from said boss end to said other end.
3. The yoke of claim 1, in which;
 a. each ear horn has a projection (15) oppositely disposed with respect to said second portion (16) for adjusting the rotational position of the ear horn.
4. The yoke of claim 1, in which;
 a. said yoke (1) is fabricated of a material having the properties of polypropylene,
 to maintain resiliency.
5. The yoke of claim 1, in which;
 a. the joints formed by the acceptance of said flexible tube (6 or 7) and said ear coupler (5)
 by said hollow ear horn are free of an adhesive.

* * * * *